(12) United States Patent
Wironen et al.

(10) Patent No.: US 7,824,702 B2
(45) Date of Patent: Nov. 2, 2010

(54) COMPOSITION FOR MAKING A BONE PASTE

(75) Inventors: John F. Wironen, Alachua, FL (US); Penelope Kao, Alachua, FL (US); Andy Bernhardt, Alachua, FL (US)

(73) Assignee: RTI Biologics, Inc., Alachua, FL (US)

( * ) Notice: Subject to any disclaimer, the term of this patent is extended or adjusted under 35 U.S.C. 154(b) by 0 days.

(21) Appl. No.: 12/026,327

(22) Filed: Feb. 5, 2008

(65) Prior Publication Data

US 2008/0124397 A1   May 29, 2008

Related U.S. Application Data (63) Continuation of application No. 09/976,556, filed on Oct. 11, 2001, now abandoned.

(51) Int. Cl.
 A61F 2/00   (2006.01)
 A61F 2/28   (2006.01)
(52) U.S. Cl. .............. 424/423; 424/422; 523/115; 623/23.61; 623/23.63
(58) Field of Classification Search ............... 424/422, 424/423; 523/115; 623/23.61, 23.63
 See application file for complete search history.

(56) References Cited

U.S. PATENT DOCUMENTS

| | | | |
|---|---|---|---|
| 3,595,675 A * | 7/1971 | Ash et al. .................. 426/576 |
| 3,737,973 A | 6/1973 | Stawski |
| 3,914,419 A | 10/1975 | Haeger et al. |
| 4,013,073 A | 3/1977 | Cunningham |
| 4,018,222 A | 4/1977 | McAleer et al. |
| 4,127,126 A | 11/1978 | Schunk |
| 4,243,080 A | 1/1981 | Choksi et al. |
| 4,410,321 A | 10/1983 | Pearson et al. |
| 4,496,468 A | 1/1985 | House et al. |
| 4,540,410 A | 9/1985 | Wood et al. |
| 4,551,135 A | 11/1985 | Gorman et al. |
| 4,610,672 A | 9/1986 | Ewalt et al. |
| 4,652,440 A | 3/1987 | Paik et al. |
| 4,671,410 A | 6/1987 | Hansson et al. |
| 4,697,584 A | 10/1987 | Haynes |
| 4,743,229 A | 5/1988 | Chu |
| 4,804,744 A | 2/1989 | Sen |
| 4,820,306 A | 4/1989 | Gorman et al. |
| 4,871,261 A | 10/1989 | Randklev |
| 5,114,240 A | 5/1992 | Kindt-Larsen et al. |
| 5,215,536 A | 6/1993 | Lampropoulos et al. |
| 5,370,221 A | 12/1994 | Magnusson et al. |
| 5,398,483 A | 3/1995 | Smith et al. |
| 5,405,390 A | 4/1995 | O'Leary et al. |
| 5,484,410 A | 1/1996 | Kriesel et al. |
| 5,588,745 A | 12/1996 | Tanaka et al. |
| 5,645,347 A | 7/1997 | Draenert |
| 5,651,372 A | 7/1997 | Caillouette |
| 5,660,849 A | 8/1997 | Polson et al. |
| 5,707,962 A | 1/1998 | Chen et al. |
| 5,739,176 A | 4/1998 | Dunn et al. |
| 5,766,149 A | 6/1998 | Kriesel et al. |
| 5,779,668 A | 7/1998 | Grabenkort |
| 5,817,055 A | 10/1998 | Ljungquist |
| 5,910,315 A | 6/1999 | Stevenson et al. |
| 5,951,160 A | 9/1999 | Ronk |
| 6,022,324 A | 2/2000 | Skinner |
| 6,030,635 A | 2/2000 | Gertzman et al. |
| 6,116,773 A | 9/2000 | Murray |
| 6,179,815 B1 | 1/2001 | Foote |
| 6,180,605 B1 | 1/2001 | Chen et al. |
| 6,349,850 B1 | 2/2002 | Cheikh |
| 6,394,975 B1 | 5/2002 | Epstein |
| 6,679,918 B1 | 1/2004 | Benedict et al. |
| 2001/0018614 A1 | 8/2001 | Bianchi |

FOREIGN PATENT DOCUMENTS

| | | |
|---|---|---|
| DE | 2921565 A1 | 12/1980 |
| EP | 0266058 | 5/1988 |
| EP | 0800837 | 10/1997 |
| FR | 861474 A | 2/1941 |
| FR | 2749169 | 12/1999 |
| WO | WO9718031 | 5/1997 |
| WO | WO9840113 | 9/1998 |

OTHER PUBLICATIONS

Communication Relating to the Results of the Partial International Search from PCT/US02/05903, dated Sep. 27, 2002.

(Continued)

Primary Examiner—Taeyoon Kim
(74) Attorney, Agent, or Firm—McAndrews, Held & Malloy, Ltd.

(57) ABSTRACT

Disclosed herein is an efficient and cost-effective system for reconstituting bone pastes comprising a first syringe containing a reconstitution fluid and second syringe containing paste components, wherein said first and second syringes are communicatingly interconnectable. Also disclosed are novel methods for producing and storing bone pastes. Alternatively, a mixing syringe is disclosed, which is useful for reconstituting a paste, inter alia, comprising a flexible midportion, whereby repeated compression of the flexible midportion results in mixing the contents of the syringe.

10 Claims, 12 Drawing Sheets

OTHER PUBLICATIONS

International Publication No. WO 01/47571 A2 (PCT/US00/35572), International Publication Date Jul. 5, 2001 for System for Reconstituting Pastes and Methods of Using Same, Inventors: Wironen, et al., Published without International Search Report.

International Publication No. WO 01/47571 A3 (PCT/US00/35572), International Publication Date Jul. 5, 2001 for System for Reconstituting Pastes and Methods of Using Same, Inventors: Wironen, et al., Published with International Search Report.

International Preliminary Examination Report for PCT/US00/35572, Completed May 16, 2002, Submitted for the Demand Jul. 26, 2001.

Zhang et al., "Effect(s) of the Demineralization Process on the Osteoinductivity of Demineralized Bone Matrix." J. Periodontal. 68(11):1085-1092 (1997).

Vail et al., "Equine Demineralized Bone Matrix: Relationship Between Particle Size and Osteoinduction," Veterinary Surgery 23:386-395 (1994).

* cited by examiner

COMPOSITION FOR MAKING A BONE PASTE

CROSS-REFERENCE TO RELATED APPLICATIONS

This application is a continuation of U.S. patent application Ser. No. 09/976,556, filed Oct. 11, 2001, now abandoned and claims the benefit of such application under 35 USC §120.

BACKGROUND OF THE INVENTION

The ability to preserve biomedical substances has a great impact on the usefulness and applicability of such substances. This is especially true for important liquid or semi-solid substances whose vital components are prone to degradation and/or spoiling when left in liquid form for extended periods of time. One method routinely utilized for preserving liquid or semi-solid substances involves the removal of the aqueous component of such substances (e.g. freeze-drying) to produce a dry powder. While converting liquid substances into powder form may address the problems of degradation and spoiling, problems still arise as to how to reconstitute such powders back into usable liquid form in a convenient and practical fashion.

An example of an increasingly important biomedical substance is osteogenic Bone Paste (WO 98/40113). Osteogenic Bone Paste has provided surgeons with a revolutionary means for repairing serious bone defects, as well as other bone-related injuries and problems. While current methods of utilizing bone paste have shown promise, there is a constant need for devising new, cost-effective techniques of storing and preserving bone paste and other biomedical substances, which, in turn, will increase their usefulness and adaptability to medical applications.

SUMMARY OF THE INVENTION

The subject invention concerns a system that allows for a more expeditious and facile use and preparation of pastes. Specifically exemplified is a novel system for reconstituting bone paste, and/or other biomedical pastes or powders, that results in decreasing the time involved in processing such pastes, as well as diminishing the costs and inefficiencies associated with their storage. One aspect of the subject invention pertains to a system that comprises a first syringe containing reconstitution liquid and a second syringe containing paste components, wherein said first and second syringes are communicatingly interconnectable.

Another aspect of the subject invention pertains to a method of reconstituting a paste that comprises obtaining a first syringe that contains reconstitution liquid; obtaining a second syringe that contains paste components; and contacting (e.g. mixing) the contents of the first syringe with the contents of the second syringe.

A further aspect of the subject invention pertains to an article of manufacture comprising a syringe containing paste components under a vacuum.

Yet another aspect of the subject invention pertains to a kit comprising a first syringe containing reconstitution liquid, a second syringe containing paste components, and packaging materials.

Further still, another aspect of the subject invention pertains to a storing method for bone pastes that provides long-shelf life and simple implementation of the stored bone paste.

Further still, another aspect to the subject invention pertains to a mixing syringe that comprises a barrel having a first and second ends and a midsection that comprises a flexible portion. When contents are put in the mixing syringe, they can be easily mixed by squeezing the flexible portion by hand or by appropriate mechanical devices known in the art.

The subject invention provides an easy means for preparing pastes for utilization in medical and/or dental procedures. In addition, the subject invention cuts down on the costs of preserving bone and/or other biomedical pastes, and extends their shelf life. With respect to graft pastes, current methods require that they are stored at extremely cold temperatures (−80° C.). Such freezing presents a number of problems. Refrigeration at these temperatures is very costly, and the handling of the pastes at this temperature can be very time consuming. Also, extremely careful attention is required to ensure that the integrity of the paste is maintained. In contrast, the subject invention allows the graft paste to be processed down to its critical components, for example, by freeze-drying, and provides a simple means to reconstitute the paste components back into a workable paste, immediately before surgery. Processing the graft paste into its critical components allows for the storage of the paste at ambient (room) temperature for extended periods of time.

The subject invention also pertains to freeze-dried compositions that possess osteogenic, chondrogenic or chondroprotective, or other beneficial properties. The subject dried paste compositions are capable of being stored at room temperature and retaining their osteogenic, chondrogenic, or chondroprotective properties upon reconstitution.

The ability to store freeze-dried bone pastes at room temperature and then reconstitute the paste prior to surgery is one of the primary advantages of the subject invention. These and other advantageous aspects of the subject invention are described in further detail below.

DESCRIPTION OF THE DRAWINGS

FIG. 1 shows a side view of a disassembled apparatus for reconstituting pastes according to the principles of the subject invention, including a first syringe having a male connector end (FIG. 1A) and a second syringe having a female connector end (FIG. 1B).

FIG. 10 shows a side view 10A and a perspective view 10B of an embodiment of the invention pertaining to a plunger comprising an aperture and channel to facilitate expulsion of air from the contents of a syringe.

FIG. 11 shows a side view of a mixing syringe, disassembled (FIG. 11A) and assembled (FIG. 11B), having a flexible midsection to facilitate mixing of its contents.

FIG. 12 shows a side view of another version of the mixing syringe, disassembled (FIG. 12A) and assembled (FIG. 12B), wherein the plunger of the syringe has a larger end for stabilizing a portion of the flexible midsection.

FIG. 13 shows a longitudinal cross-section of a first configuration (FIG. 13A) of the first end of the barrel shown in FIGS. 11 and 12; a second configuration (FIG. 13B) representing a transverse cross-section along line AA; and a third configuration (FIG. 13C) which is shorter in length.

DETAILED DISCLOSURE OF THE INVENTION

Definitions

The term "communicatingly interconnectable" as used herein refers to the ability of two or more syringes to be connected in such as way as to allow the contents of a given syringe to be transferred to another syringe.

The term "paste" as used herein refers to a malleable composition useful in medical procedures. Pastes for use with the principles of the invention include, but are not limited to allograft pastes (e.g., osteogenic pastes or chondrogenic pastes), carrier associated Growth Factors, carrier associated mineralized particles, morsellized skin or other tissue, Fibrin powder, Fibrin/plasminogen glue, biomedical plastics, Demineralized Bone Matrix (DBM)/glycerol, cortico cancellous chips (CCC), DBM/pleuronic F127, and DBM/CCC/F127, human tissue/polyesters or polyhydroxy compounds, or polyvinyl compounds or polyamino compounds or polycarbonate compounds or any other suitable viscous carrier; or alpha-BSM® or polyethylene oxide, polyvinvylpyrrolidone, polyvinyl alcohol, collagen and dextran. Preferably, pastes used in accordance with the principles of the subject invention are graft pastes having osteogenic or chondrogenic properties. Furthermore, the paste components can include other materials such as, but not limited to, antibiotics, sucrose, dextrose or other biologically compatible anti-caking agents, and optionally, barium, iodine, or other high atomic weight elements for purposes of radioopacity.

In a most preferred embodiment, the paste for use as taught herein contains a carrier, an osteoconductive component, and an osteoinductive component. Carriers can include, but are not limited to, gelatin, collagen, glycerol, hyaluronic acid, chondroitin sulfate, polyethylene oxide, polyvinvlypyrrolidone, polyvinyl alcohol, dextran and/or mixtures thereof. Osteoconductive materials suitable for use with the subject invention include, but are not limited to, hydroxapatite (HA), tricalcium phosphate (TCP), CCC, bioactive glass, bioactive ceramics, and/or mixtures thereof. Osteoinductive materials suitable for use with the subject invention include, but are not limited to, DBM, and growth factors such as bone morphogenic protein (BMP), TGF-beta, PDGF, and/or mixtures thereof.

The term "paste components" as used herein refers to those components of a paste that are produced by removing liquid from a paste, and are capable of reconstitution into a workable paste upon contact with a reconstitution liquid. One skilled in the art will readily appreciate processing methods suitable in accord with the principles of the subject invention. Preferably, paste components are those components produced by removing water from a paste of interest, such as, but not limited to, by freeze-drying of a paste.

The term "reconstitution liquid" as used herein refers to a liquid capable of reconstituting paste components into a workable paste upon mixing with the paste components. Reconstitution liquids useful in accordance with the principles of the subject invention include, but are not limited to, water and water-based salines, or any other non-toxic fluid such as blood, Growth Factor solutions, antibiotic solutions, protein solutions, gelatin solutions, analgesic solutions, synovial fluid and platelet rich plasma. In a preferred embodiment, the reconstitution fluid is blood, or fractions thereof (e.g., serum or plasma). More preferably, paste components are reconstituted with a patient's blood to form a paste that is implanted back into the patient.

The term "syringe" as used herein refers to an apparatus that comprises a barrel and plunger, which is capable of containing a substance, and ejecting that substance at a desired site. In a preferred embodiment, two or more syringes are connectable with each other, and are capable of sending and receiving their contents to and from each other. The mode of actuating the transfer of a syringe's contents can be by hand, but can include other mechanical means, for example, by a motor. In an even more preferred embodiment, the syringe is capable of holding its contents under a vacuum, preferably, up to 5 years or more. Further, as discussed above, the syringes are preferably communicatingly interconnectable. One means of connection includes, but is not limited to, the presence of a male Luer-type connector on a first syringe and a female Luer-type connector on a second syringe. The presence of this reciprocal male and female connection not only provides for a simple and efficient interconnection, but decreases undesirable "dead" space between the two syringes. Other means of connection will be readily appreciated by those skilled in the art, such as, for example, a stopcock for receiving two male connectors or a two-sided female adapter for receiving two male connectors.

Figure 1A:
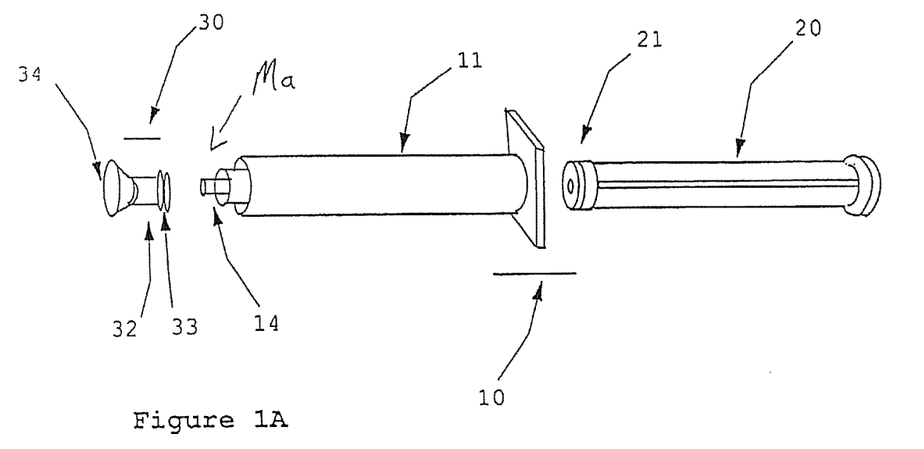
Figure 1B:
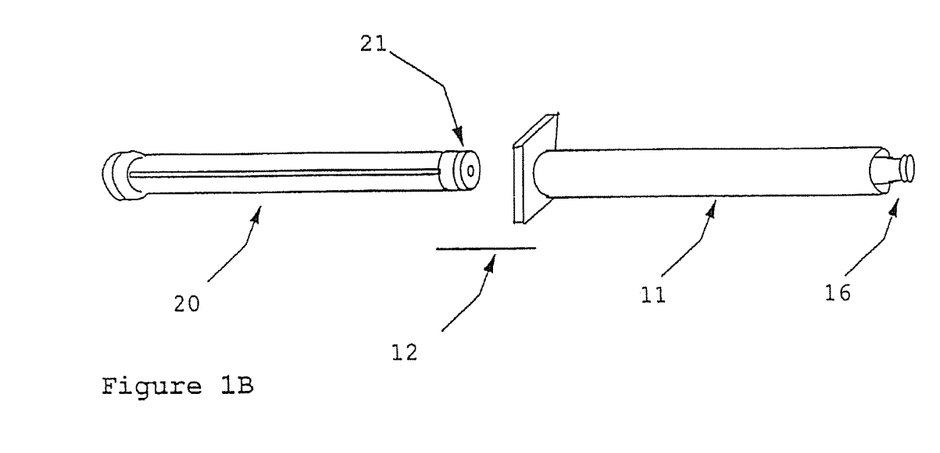
Figure 2:
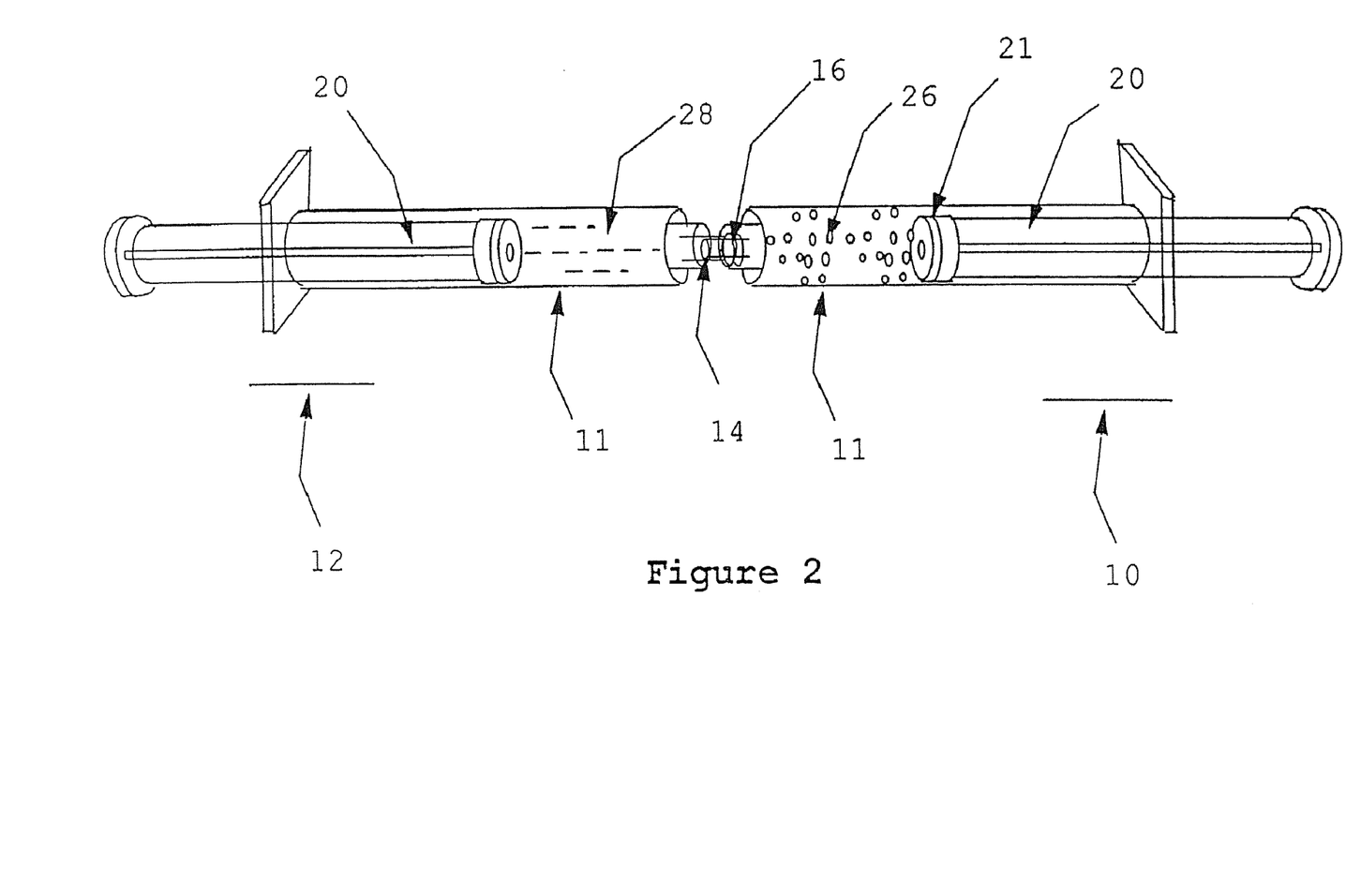
FIG. 2 shows a longitudinal cross-section of the assembled apparatus as shown in FIG. 1.
Figure 3:
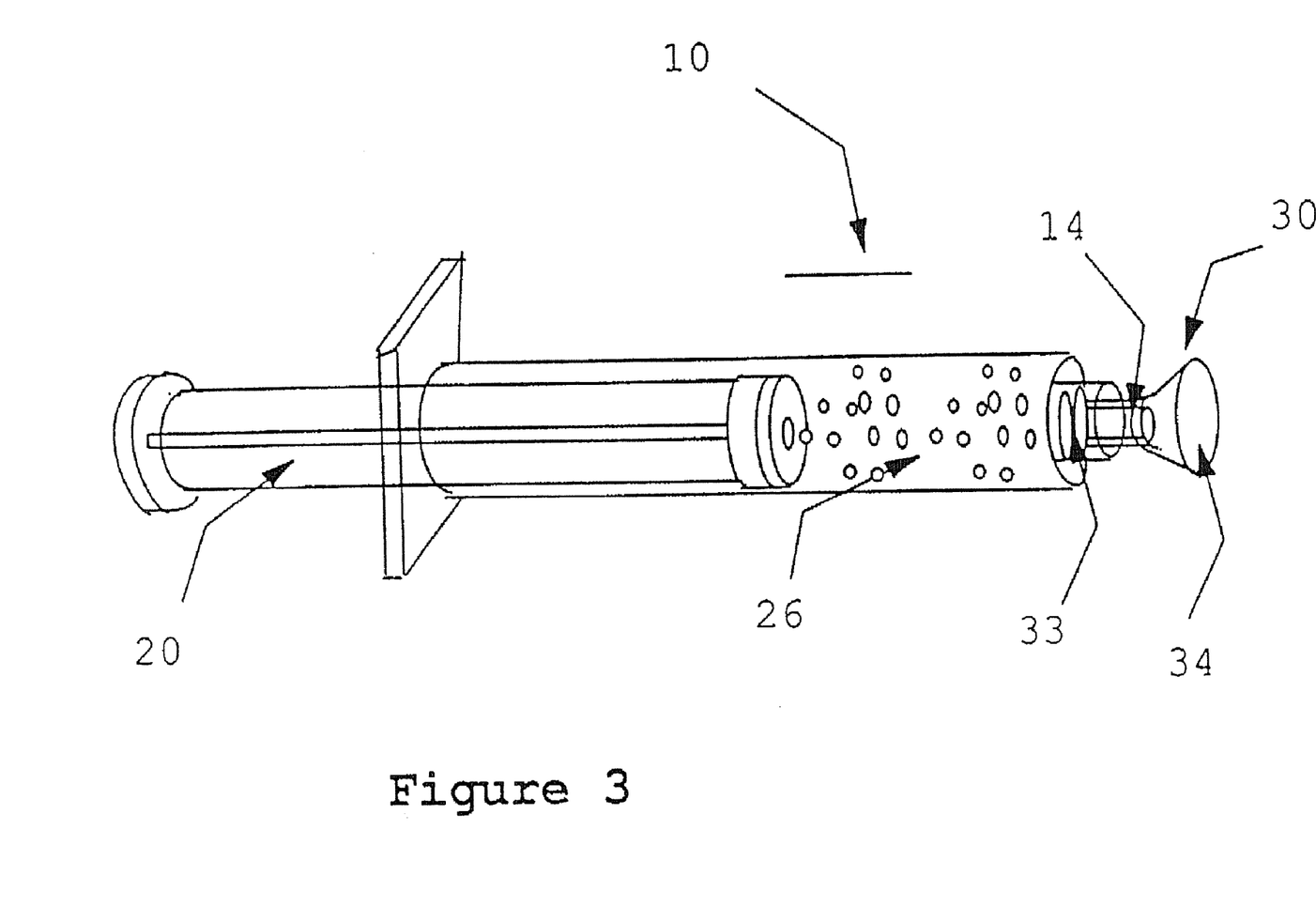
FIG. 3 shows an embodiment of the invention illustrating an assembled syringe comprising a septum cap engaged thereon for accepting a needle.

Turning now to the drawings, a reconstitution system is shown generally in FIG. 1-3. The system comprises a first syringe 10 and a second syringe 12 communicatingly interconnectable with each other. Syringes 10 and 12 comprise substantially cylindrical body portions 11, suitable for receiving a plunger rod 20. Plunger rod 20 has disposed on one end a crown 21, made of a material for forming a seal between its surface and the surface of the inner walls of the syringe body 11. Materials contemplated for the crown 21 include, but are not limited to, rubber and plastic. Second syringe 12 preferably has a female end 16 for receiving a male end 14 of first syringe 10. As shown in FIG. 2, the first syringe 10 comprises paste components 26 and the second syringe 12 comprises reconstitution fluid 28. The reciprocating male and female ends provide for a tightly sealed connection that minimizes "dead" space between the two syringes, thereby alleviating unwanted air bubbles. Alternatively, albeit less preferred, a first syringe and a second syringe may be connected by an adapter having two male ends, two female ends or a male end and female end, depending on the ends of the first and second syringes. Further, the first syringe and second syringe may be connected through friction by snapping into each other, or snapping into an adapter.

In yet another embodiment, the introduction of air is minimized in the system through the use of a stopcock valve. In this embodiment, a first syringe and a second syringe are evacuated and then communicatingly interconnected via a stopcock valve. Upon rotation of the stopcock valve, the contents of one syringe are allowed to flow into the other syringe. In light of the teachings herein, those skilled in the art will appreciate the types of valves suitable for this purpose. The important aspect of the valve is the ability to interconnect to at least two syringes.

Operation of the system to reconstitute a paste can comprise applying pressure to a first plunger rod 20 of syringe 12 which thereby pushes the reconstitution fluid 28 into syringe 10. Upon transfer of the reconstitution fluid 28, it is brought into contact with the paste components 26. Preferably, the plunger rod 20 in syringe 10 is gradually pulled in coordination with the pushing of rod 20 in syringe 12 to create negative pressure and more space in syringe 10 to aid in and accommodate the transfer of the reconstitution fluid 28. In a preferred embodiment, the paste components are inserted into syringe 10, and syringe 10 is evacuated such that the paste components are held under a vacuum. Once an adequate amount of reconstitution fluid is transferred from syringe 12 to syringe 10, the contents of syringe 10 can be transferred back to syringe 12 whereby the paste components and reconstitution fluid are mixed resulting in a useable paste. Preferably, the contents of each syringe are transferred several times until the desired consistency of the paste is achieved.

As shown in FIG. 3, another embodiment of the invention is directed to a system for reconstituting pastes comprising a first syringe 10 containing paste components 26 held under a vacuum and a removable cap 30. The removable cap 30 comprises a rigid portion 33 that is engaged to the end of the syringe 10 and a septum portion 34. The rigid portion preferably includes an end 33 configured to be removably engageable to the end of a syringe. More preferably, the end 33 is a male or female connecting end. The septum portion is preferably made of a material that is capable of accepting an injection means (for example, a needle; see U.S. Pat. No. 5,951,160 for other examples of injection means) while still maintaining the seal of the syringe 10, such as, but not limited to, rubber, silicone, plastic and other elastic materials.

Figure 4:
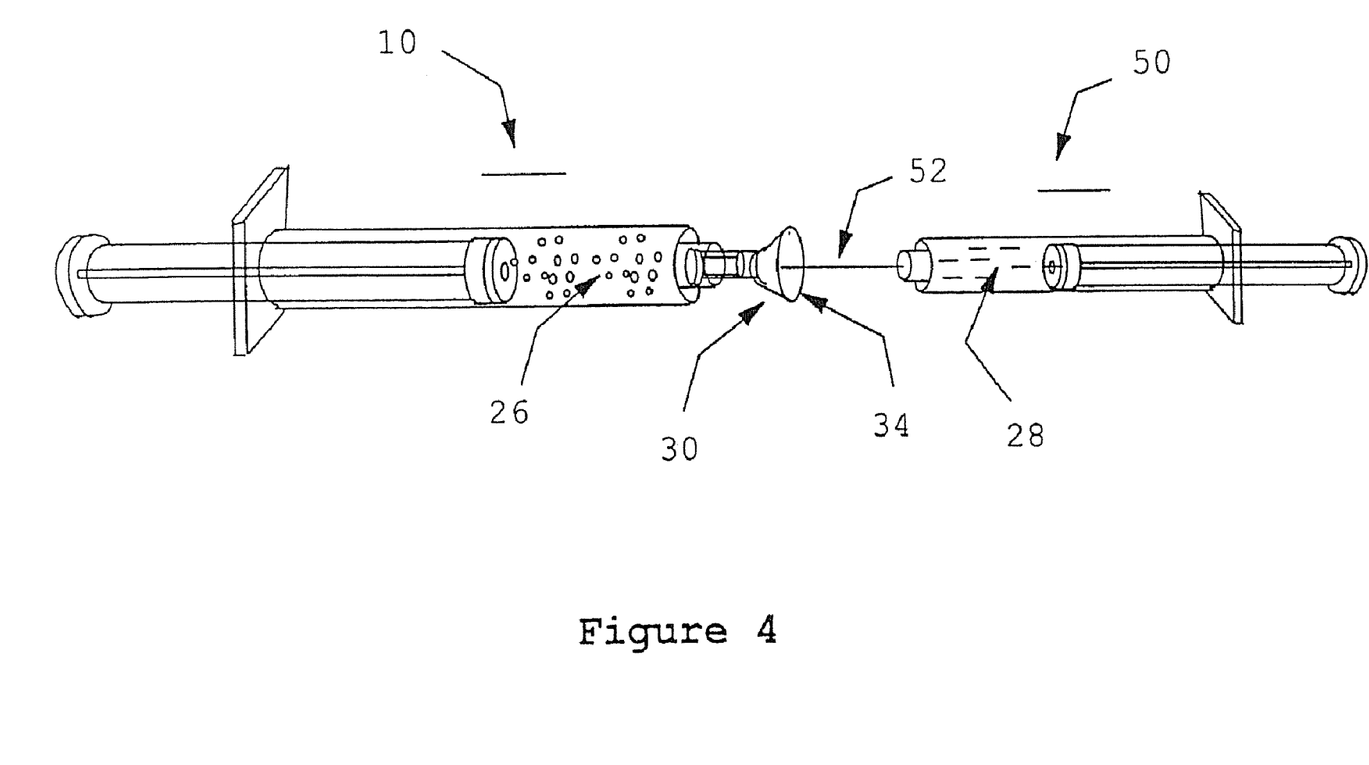
FIG. 4 shows an embodiment of the invention illustrating the assembled syringe of FIG. 3 accepting a needle for the transfer of reconstitution fluid.

A further embodiment shown in FIG. 4 pertains to a system for reconstituting pastes. Operation of this embodiment involves drawing reconstitution fluid into a syringe 50 equipped with a needle 52 on its end. The needle 52 is inserted into syringe 10 through the septum portion 34 of the cap 30 and the reconstitution fluid 28 is transferred into the syringe 10. Preferably, the reconstitution fluid 28 is transferred while the transfer of any air is avoided. Once the reconstitution fluid 28 is transferred into syringe 10, the cap 30 is removed, at which time a second syringe is interconnected with syringe 10. The paste components and reconstitution fluid present in syringe 10 are mixed by transfer back and forth from syringe 10 to the second syringe until a paste of a desired consistency is formed. In a preferred embodiment, the paste components comprise a gelatin material which is melted by heating prior to mixing. Preferably, heating may occur in a water bath for 3 to 5 minutes. After the paste is formed, the syringe 10 and the second syringe are dissociated, and the paste is ejected as needed.

Figure 5:
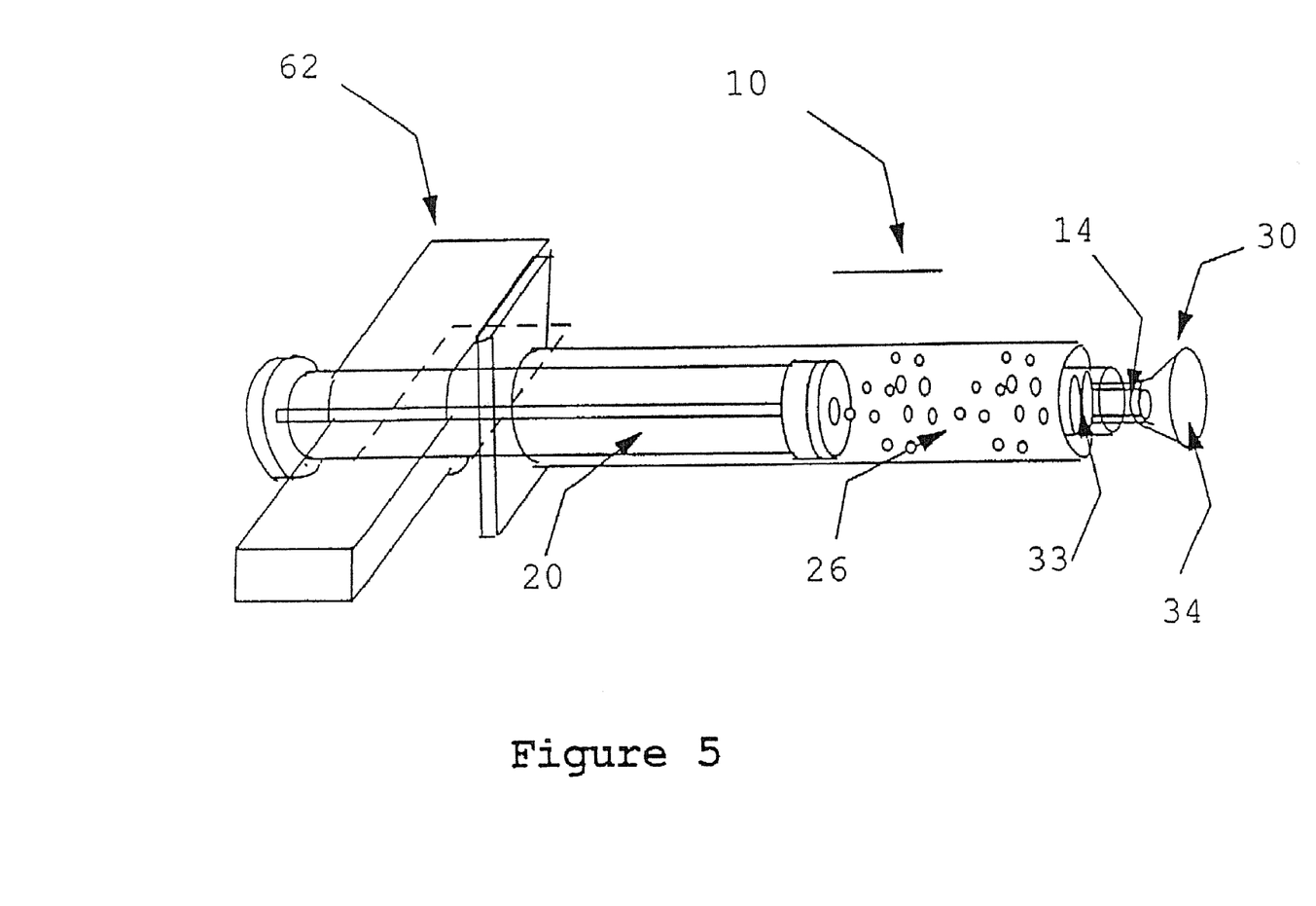
FIG. 5 shows a side view of an embodiment of the invention illustrating a syringe with a depression interlock disposed thereon for securing the syringe.

In another embodiment, as shown in FIG. 5, the subject invention is directed to an article of manufacture that comprises a syringe 10 that contains paste components 26 being held under a vacuum. To aid in preventing the inadvertent release of the vacuum, a depression interlock 62 is provided that protects the plunger rod 18 from sliding. Alternatively, the syringe comprises a cap 30 engaged at one end. The cap 30 preferably comprises a rigid portion 33 and a septum portion 34. Those skilled in the art will readily appreciate, in light of the teachings herein, other devices suitable for preventing the inadvertent depression of the plunger rod.

Figure 6:
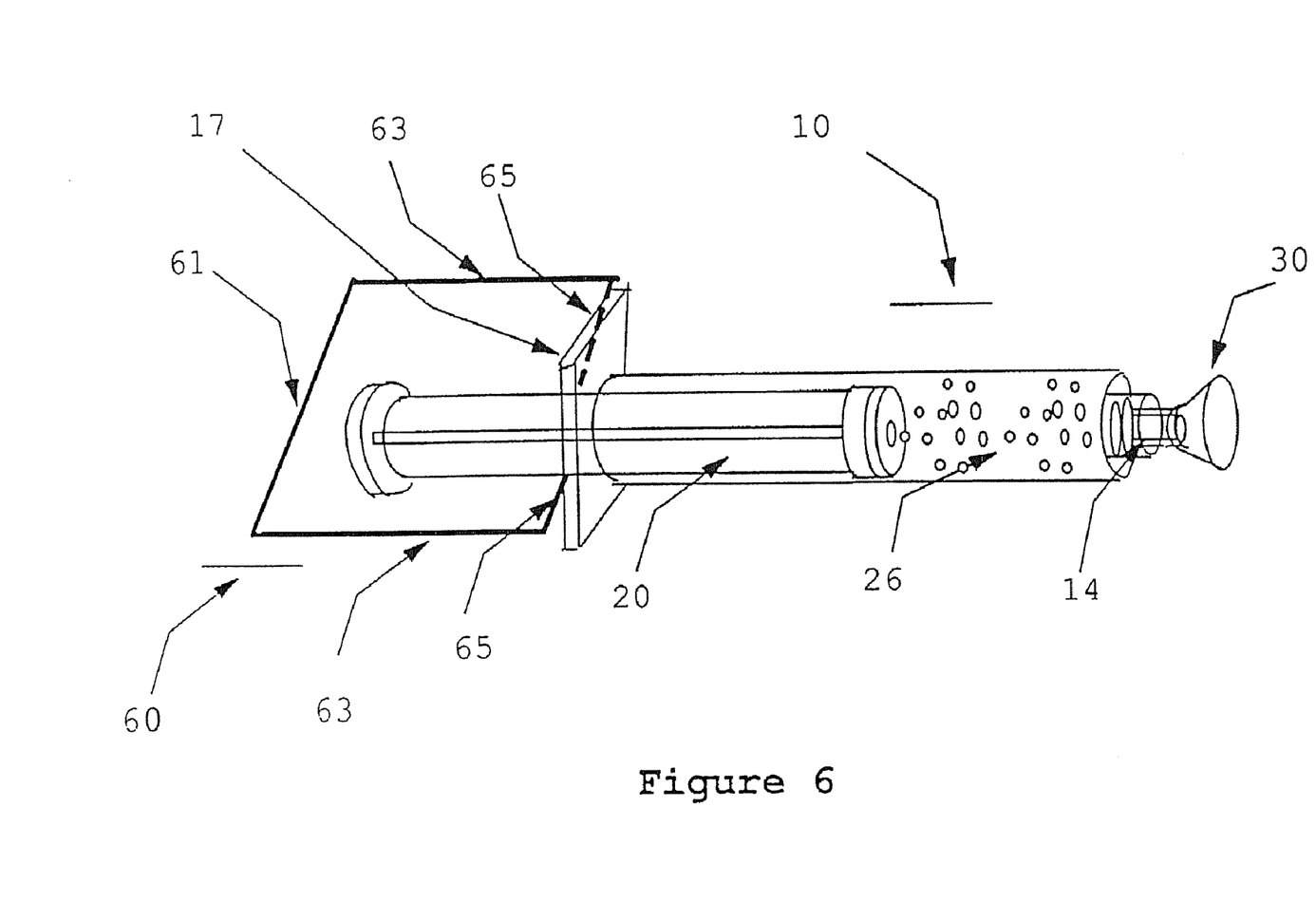
FIG. 6 shows a side view of an embodiment of the invention illustrating a syringe with a guard rack designed for aiding the loading of paste components into the syringe.

A further embodiment of the subject invention is directed to kit comprising a first syringe containing paste components, a second syringe, and a container for housing the syringes. Preferably, the second syringe contains reconstitution fluid. In a more preferred embodiment, the kit comprises a cap that has a rigid portion for engaging a syringe and a septum for accepting a needle. In an even more preferred embodiment, the kit comprises a needle having an end for engaging a syringe. Alternatively, FIG. 6 shows an embodiment of the invention that is directed to a process for packing paste components into a syringe. Paste or paste components 26 are placed within a syringe 10 having disposed thereon a guard rack 60 having a bottom 61, two or more sides 63, and two or more top portions 65 extending perpendicularly from the ends of the sides 63 that are opposite the bottom 61. The top portions 65 preferably extend toward each other such that a space is formed between the two extended top portions 65 that is of a suitable size to accommodate a plunger rod 20 and support the bottom end 17 of the syringe 10. To produce an evacuated syringe, a cap 30 is placed loosely onto the top end 14 of the syringe 10, and the syringe 10 disposed on the guard rack 60 is placed in a lyophilizer. Upon lyophilization of the contents in the syringe 10, the syringe 10 and guard rack 60 is raised such that the cap 30 comes into contact with a roof surface of the lyophilizer. The cap 30 is contacted with a force sufficient to firmly engage the cap 30 onto the syringe 10, to thereby form and maintain a vacuum. Alternatively, a valve is removably engaged to said syringe. The configuration of the guard rack 60 and the syringe 10 prevents the depression of the plunger rod during loading of the syringe 10. Those skilled in the art will readily appreciate, in view of the teachings herein, other devices suitable for preventing depression of the plunger rod such as the depression interlock discussed above.

Figure 7:
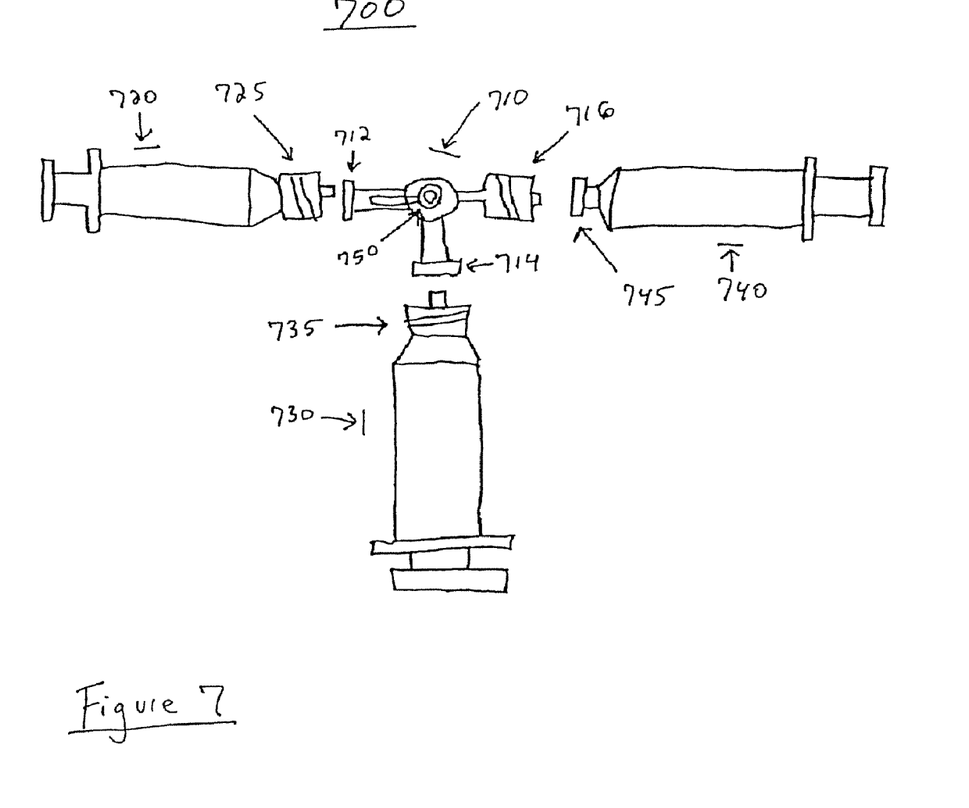
FIG. 7 shows a side view of an embodiment of the invention tailored for reconstituting larger quantities of paste components that comprises a three-way valve coupler.

FIG. 7 shows a further embodiment 700 of the invention that is especially tailored to reconstitute larger quantities of paste components. Embodiment 700 comprises a three-way valve coupler 710 that has three Luer-lok adapter ends: a first female end 712, a second female end 714, and a male end 716 that are interconnectable with corresponding Luer-lok ends on a first syringe 720 having a male end 725, a second syringe 730 having a male end 735, and a third syringe 740 having a female end 745, respectively. Those skilled in the art will recognize that the Luer-lok adapter ends of the three-way valve coupler 710 are readily interchangeable with either male or female Luer-lok ends. The three-way valve coupler 710 is equipped with a rotatable valve 750 (preferably a conventional Qosina valve) that is capable of directing communication between two of three adapter ends. In a preferred embodiment, first syringe 720 and third syringe 740 are 5 cc syringes and second syringe 730 is a 20 cc syringe.

The preferred operation of embodiment 700 is as follows: Syringes 720, 730, and 740 are connected to the three-way valve coupler 710. Syringe 720 contains reconstitution fluid, syringe 740 contain paste components, and syringe 730 is empty. Rotatable valve 750 is turned to 9 o'clock (as shown) to close flow to syringe 720 and opening flow between syringes 730 and 740. The plunger 755 of syringe 730 is pulled to draw air out of paste components contained in syringe 740. After removing air, syringe 730 can be removed and rotatable valve 750 is turned to open flow between syringes 720 and 740. The plunger 760 of syringe 720 is pushed and the plunger 765 of syringe 740 is pulled to draw reconstitution fluid into syringe 740. The contents of syringe 740 is then transferred back to syringe 720 and back to syringe 740, and repeated if necessary, to mix the reconstitution fluid with the paste components, until desired mixture is achieved.

Figure 8:
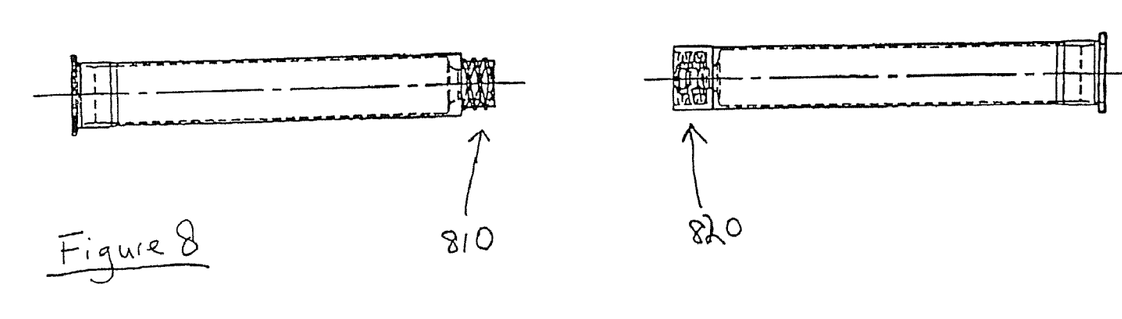
FIG. 8 shows a side view of an embodiment of the invention comprising interconnectable syringes having larger bores and fasteners.
Figure 9:
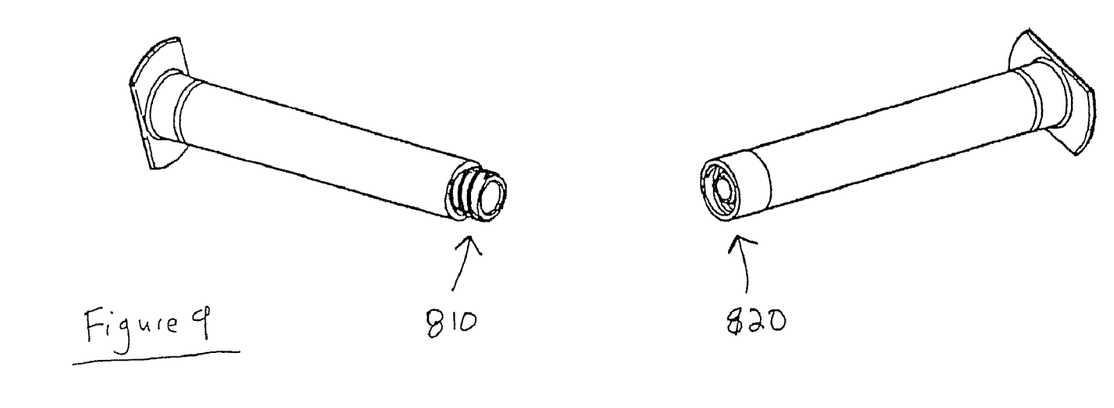
FIG. 9 shows a perspective view of the embodiment shown in FIG. 8.
Figure 10A:
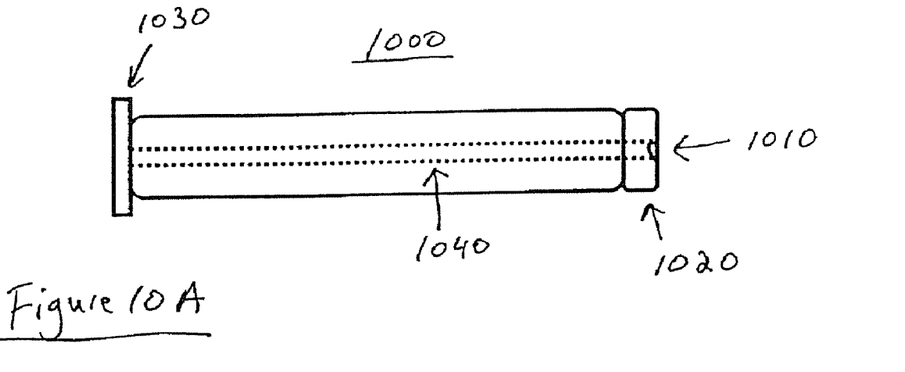
Figure 10B:
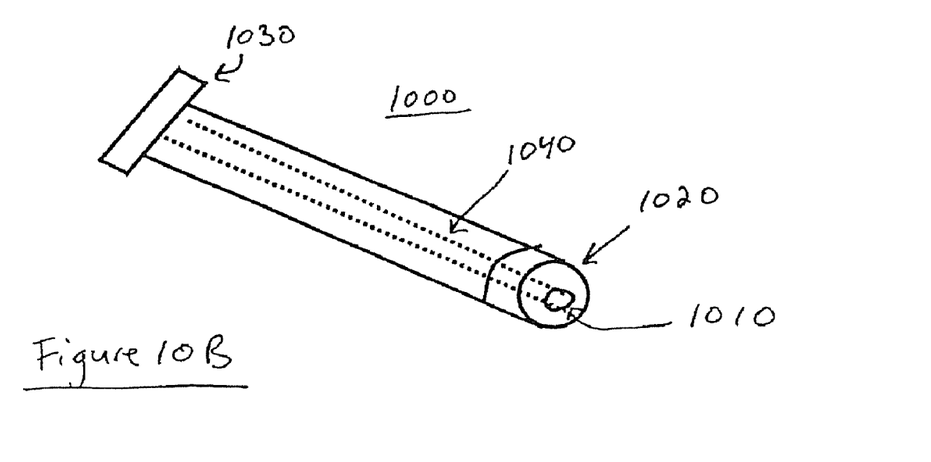

Alternatively, or preferably, when reconstituting larger quantities of paste components, syringes equipped with larger bores over standard Luer-lok ends are used to accommodate and facilitate flow of the materials to and from the syringes. FIGS. 8 and 9 represent a side view and perspective view, respectively, of syringes equipped with larger bores: female 810 and male 820. Those skilled in the art will appreciate that the ends of the syringes and three-way valve coupler shown in FIG. 7 and described above for embodiment 700, as well as the other connecting ends of devices described herein, can be substituted with ends having extra-large bores. Preferably, the extra-large bores range from about 0.4 inches to about 0.6 inches in diameter for 5-10 cc syringes. Typically, it is desirous to remove air from the paste components before, during or after reconstitution is conducted. In a specific embodiment, the removal of air is facilitated by providing an aperture in the plunger of the syringes used in accord with the teachings herein. For example, FIG. 10 shows a plunger 1000 having an aperture 1010 at its end 1020 in contact with paste components, wherein the aperture communicates with the other end of the plunger 1030 through a channel 1040 defined within the plunger 1000. Preferably, to prevent escape of paste components or reconstitution fluid, the aperture is covered with an air-permeable membrane or filled with an air-permeable plug. Materials for the plug, membrane or other similar structures are commercially available and include, for example, TF Membrane Filters, Gelman (VWR Scientific) or Porex Hydrophobic vents (Porex Corp.). According to the principles of this embodiment, as the plunger is pushed against the contents of the syringe, the pressure caused thereby acts to push the air contained in the contents through the aperture and expelled out of the syringe.

Figure 11A:
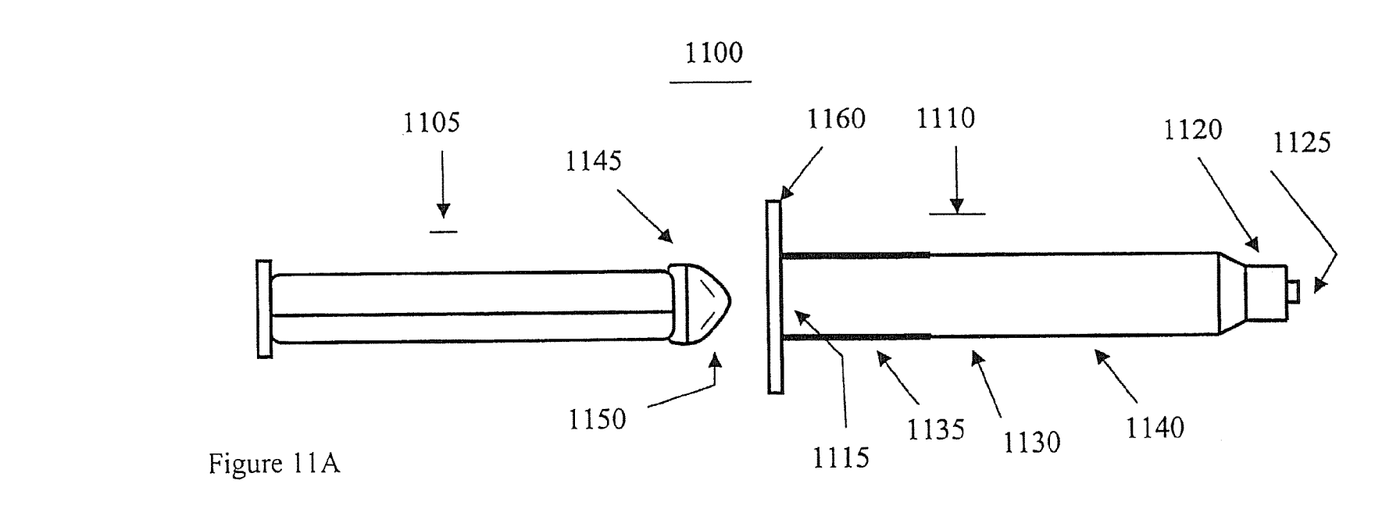

Turning to FIGS. 11A and B, an embodiment of a mixing syringe 1100 according to the teachings of the subject invention is shown, which allows for the ready mixing of its contents. The mixing syringe 1100 comprises a barrel 1110 and a plunger 1105, wherein the plunger 1105 is inserted into a second end 1115 of the barrel 1110 (see FIG. 11B). The barrel 1110 comprises a first end 1120 having an opening 1125 for extruding the mixed contents of the mixing syringe 1100 to the site of need. As shown, the first end 1120 is configured as a luer-lok connector, which would allow engagement with another luer-lok connector. In a preferred embodiment, the mixing syringe 1100 is provided with one or more paste components and a reconstitution fluid is provided into the mixing syringe 1100 through the first end 1120, by, for example, connection of a syringe or other device containing said reconstitution fluid. However, those skilled in the art will appreciate that the first end 1120 can have a number of different connecting means securely attached, or integral thereto, such as a threaded neck and cap, valve or a septum, which may or may not be removable. Between the first end 1120 and second end 1115 of the barrel 1110 is a midsection 1130 comprising a rigid portion 1135 and a flexible portion 1140. Preferably, as shown, the rigid portion 1135 is proximate to said second end 1115, meaning closer to the second end 1115 than the first end 1120. When two or more substances are disposed within the mixing syringe 1100, and with the plunger 1105 situated within the barrel 1110, the two or more substances are mixed by squeezing the flexible portion 1140, preferably repeated squeezing. The rigid portion 1135, which is part of or proximate to the second end 1105, helps maintain the structural integrity of the barrel during mixing. The mixing syringe 1100 is also provided with a flange 1160 to help manipulate the mixing syringe 1100 during extrusion of the mixed contents. The flange is preferably made of a rigid material. To aid in minimizing the dead space within the barrel 1110 of the mixing syringe 1100, the insertion end 1145 of the plunger 1105 has a tapered tip 1150. Naturally, those skilled in the art will appreciated that the insertion end of the plunger may take a number of different shapes, such as a flat end, rounded end, conical, etc.

Figure 11B:
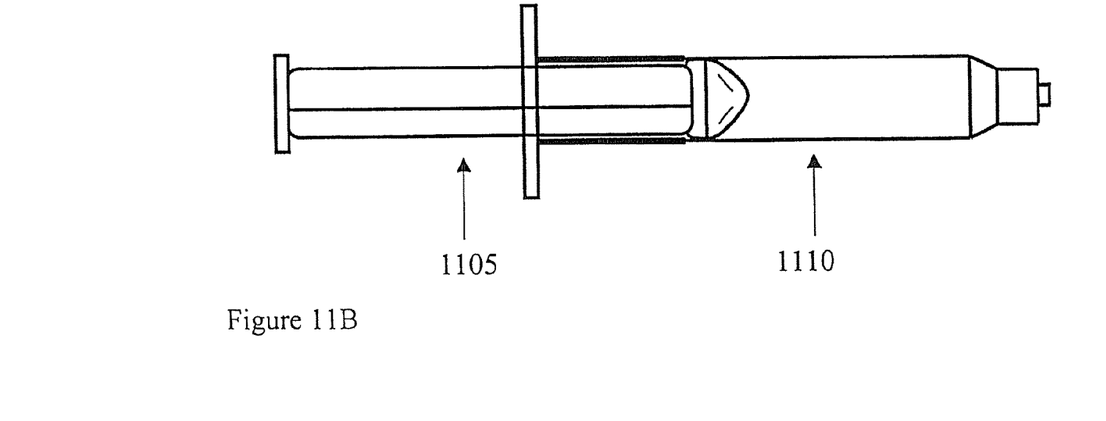

The flexible portion 1140 should be adequately flexible to be compressible by hand. Those skilled in the art will readily appreciate materials suitable for producing the flexible portion. Examples of appropriate materials include, but are not limited to, low density polymers such as low density polyethylene, silicone, laminate plastics, polyurethane, Krayton, rubber latex and other suitable flexible elastic materials. If it is desired to use a mechanical device for squeezing the flexible portion 1140, the flexibility of the flexible portion 1140 may be increased or decreased depending on the desired mode of squeezing, with the proviso that some level of flexibility should be maintained. The rigid portion 1135 is made from a more rigid material, such as, for example polypropylene. Other conventional materials suitable for making the rigid portion will be readily appreciated by those skilled in the art. The mixing syringe can be made according to several conventional manufacturing techniques, e.g., injection molded, dipping molded, rotational molded, or blow molded.

Upon mixing the contents of the mixing syringe 1100, the contents are extruded out of the opening 1125 at the first end 1120 to the site of need by applying force to the plunger 1105. As mentioned above the first end 1120 may have a number of different connectors securely attached, or integral to the first end 1120, such as, Luer-lok connector (friction-fit or screw-type), threaded neck with attachable cap, smooth neck with slip-fit cap, septum, one-valve, multiple-way valve. It is preferred that the dimensions of the opening are smaller than the dimensions of the inner surface of the barrel 1110, thereby providing a smaller end that governs the flow of contents out of the syringe. However, depending on the ultimate end-use, the first end 1120 can be cut or pre-scarred such that the tip of the first end 1120 is removed, thereby forming a straight-walled open-ended barrel. Naturally, the straight-walled open ending is preferred for applications requiring a high flow rate of delivery, or where a larger sized mass of mixed contents is desired, or where larger bone particles or chips are mixed in the mixing syringe. Furthermore, the need to vent air in the mixing syringe is less of an issue because mixing occurs in a single syringe and is not being transferred back and forth between syringes. Indeed, preferably, the volume of contents in the syringe is such that there is head space between the level of contents and the first end to provide room for receiving fluid. More preferred, the head space should be about 0-1 inches.

Figure 12A:
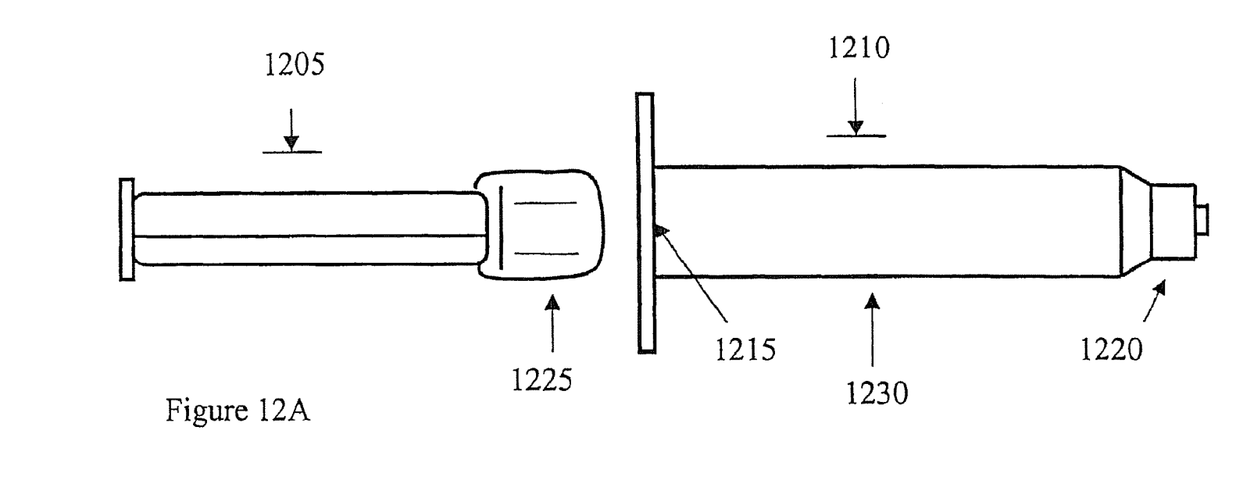
Figure 12B:
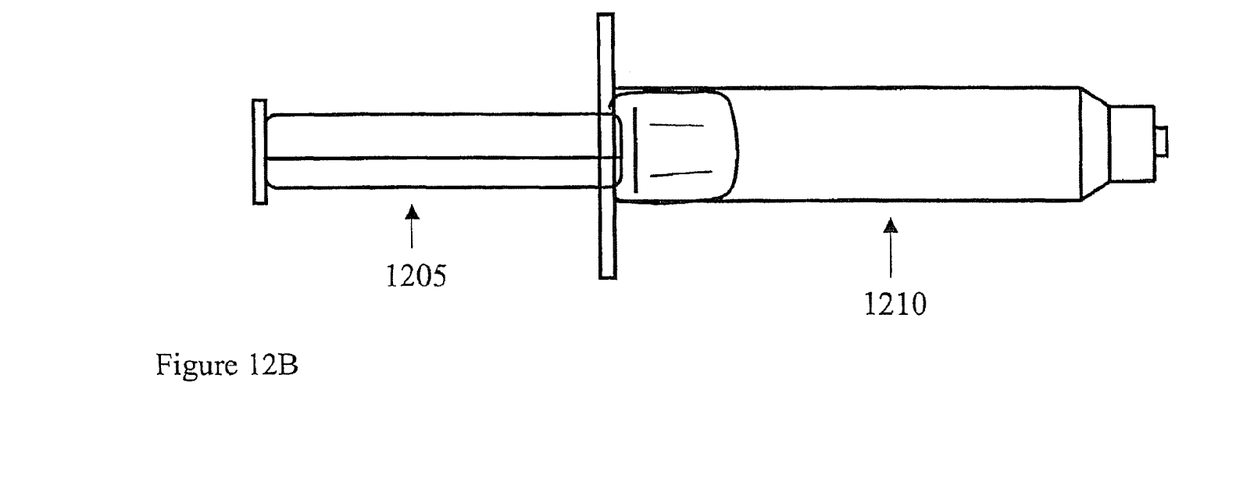

Another embodiment of a mixing syringe 1200 is shown in FIGS. 12 A and B. The mixing syringe 1200 comprises a barrel 1210 and a plunger 1205. The barrel 1210 comprises a first end 1220 and a second end 1215. The midsection 1230 is flexible and the plunger 1205 comprises a large end 1225, which upon insertion into the barrel 1210 (see FIG. 12B) acts to stabilize the flexible midsection 1230, and whereby contents within the syringe can be mixed by compression of the midsection 1230 above the position of the plunger 1205.

Figure 13A:
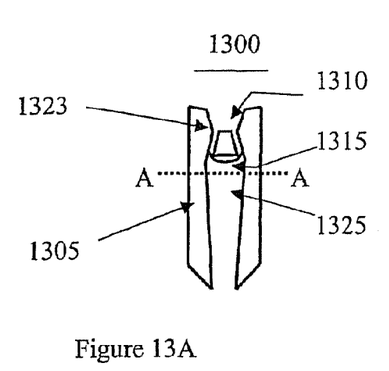
Figure 13B:
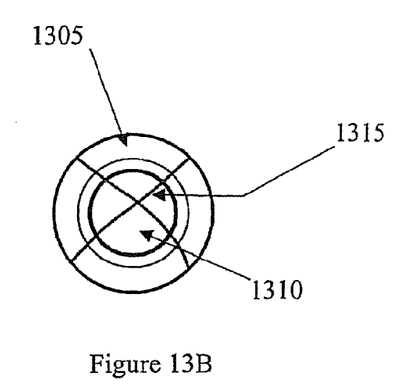
Figure 13C:
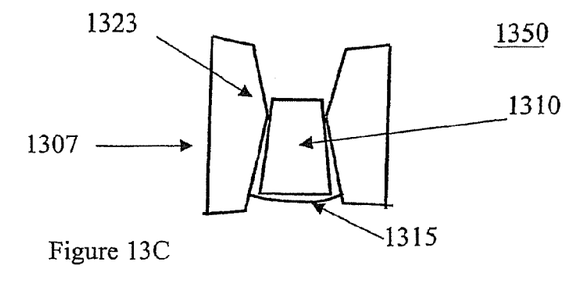
Figure 14:
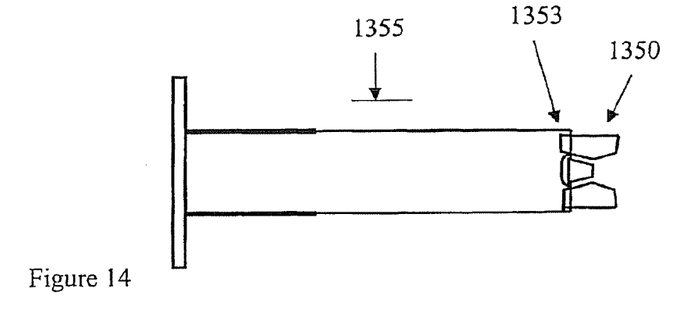
FIG. 14 shows the configuration as shown in FIG. 13C rigidly attached to the first end of the barrel of the mixing syringe shown in FIGS. 11 and 12.

FIG. 13A shows a longitudinal cross-section of an optional connector 1300 which is securely but removably attached to, or integral to, the first end of the mixing syringes shown in FIGS. 11 and 12. The connector 1300 is essentially a one-way valve that comprises a body 1305, which is generally cylindrical. The body 1305 comprises a channel 1325 formed within. The inner surface of the body defining the channel has a tapered portion 1323 which results in a narrowing of the channel 1325. A stopper 1310 is positioned in the channel 1325 such that it abuts the inner surface of the tapered portion 1323. The stopper 1310 is held in place by two flexible bands 1315 that extend across the stopper and which are attached to the body 1320. FIG. 13B represents a transverse cross-section of a connector 1300 along line AA. FIG. 13C is a connector 1350 similar to 1300 except that the body 1307 is shorter in length. FIG. 14 shows the configuration of FIG. 13C engaged to the first end 1353 of a barrel 1355 of a syringe as disclosed in FIG. 11. Upon engagement of a fluid delivery device to the connector 1300 or 1350, fluid injected into the mixing syringe pushes the stopper 1310 down which creates space between the stopper 1310 and the tapered portion 1323, thereby allowing the fluid to pass by and into the barrel 1355. As mixing occurs, contents within the mixing syringe cannot escape, as any pressure created causes the stopper 1310 to be pushed up into the tapered portion 1323. Optionally, after mixing, the connector 1350 is removed from the barrel 1355, leaving an opening out of which mixed contents can be extruded.

Example 1

Syringe A is a male Luer-lock. Syringe B is a female Luer-lock having a septum cap disposed thereon and paste components contained therein.

(1) Attach a 22-30 gauge needle to Syringe A.

(2) Draw up an appropriate amount of reconstitution fluid into syringe A, preferably blood or plasma.

(3) Plunge needle through the septum cap on syringe B and inject the reconstitution into syringe B.

(4) Warm Syringe B for 2-6 minutes in 49 degree Celsius water bath.

(5) Remove the septum cap from Syringe B. Remove the needle from syringe A.

(6) Attach Syringe A to Syringe B.

(7) Transfer the contents from Syringe A to Syringe B.

(8) Transfer the contents from Syringe B to Syringe A.

(9) Repeat steps (7) and (8) until reconstitution fluid and paste components are mixed to form a paste of a desired consistency.

(10) Use or rewarm the paste.

Example 2

The inventors have discovered that certain mix of gelatin and DBM sizes which exhibit improved osteogenicity. In a preferred embodiment, the subject invention is directed to a mixture of freeze dried DBM and gelatin, where the DBM comprises certain size ranges. In this example, the paste composition comprises freeze-dried DBM particles having a size of about 125 microns to about 850 microns. Preferably still, the DBM particles are about 250 microns to about 500 microns in size, which has exhibited enhanced osteogenicity. Furthermore, the gelatin in the paste of this example is about 125 microns to about 710 microns. Preferably still, the gelatin is about 500 to about 710 microns in size. In determining the appropriate size ranges, consideration must be given to dissolution and percolation balance: smaller particles dissolve better and larger particles provide a more balanced percolation.

In an even more preferred embodiment, the paste composition further comprises and exothermic salt, such as but not limited to, Magnesium sulfate, Magnesium chloride, Sodium sulfate, and the like. The addition of the exothermic substance causes the mixture to heat upon contact with the reconstitution fluid which aids in the dissolution of the gelatin and other components in the paste mixture.

The paste composition can be stored indefinitely at room temperature and is osteogenic upon reconstitution.

The teachings of all patents and publications cited throughout this specification are incorporated by reference in their entirety to the extent not inconsistent with the teachings herein.

It should be understood that the examples and embodiments described herein are for illustrative purposes only and that various modifications or changes in light thereof will be suggested to persons skilled in the art and are to be included within the spirit and purview of this application and the scope of the appended claims.

The invention claimed is:

1. A reconstituted paste composition comprising freeze-dried demineralized bone matrix (DBM) particles and a carrier, wherein said carrier is gelatin; wherein said freeze-dried DBM particles are about 250 microns to about 500 microns in size; wherein said gelatin is in the form of granules having a size of about 125 microns to about 710 microns; and a reconstitution fluid, wherein said reconstitution fluid is selected from the group consisting of water, water-based salines, blood, protein solutions, gelatin solutions, growth factor solutions, antibiotic solutions, analgesic solutions, platelet rich plasma, crude platelet extract, and combinations thereof.

2. The composition of claim 1, wherein said gelatin is in the form of granules having a size of about 125 microns to about 500 microns.

3. The composition of claim 1, wherein said gelatin is in the form of granules having a size of about 500 microns to about 710 microns.

4. The composition of claim 1, further comprising an osteoconductive material.

5. The composition of claim 4, wherein said osteoconductive material is selected from the group consisting of hydroxyapatite (HA), tricalcium phosphate (TCP), cortico-cancellous chips (CCC), bioactive glass, bioactive ceramics, and mixtures thereof.

6. The composition of claim 5, wherein said osteoconductive material is cortico-cancellous chips (CCC).

7. The reconstituted paste composition of claim 1, wherein said reconstitution fluid is water.

8. The reconstituted paste composition of claim 1, wherein the composition is in a container.

9. The reconstituted paste composition of claim 1, wherein the container is a syringe.

10. A method of treating a bone defect or injury comprising administering the paste composition of claim 1 to a site of need.

* * * * *